Oct. 8, 1957 H. C. SWIM Plant Pat. 1,649
PEACH TREE
Filed Nov. 6, 1956
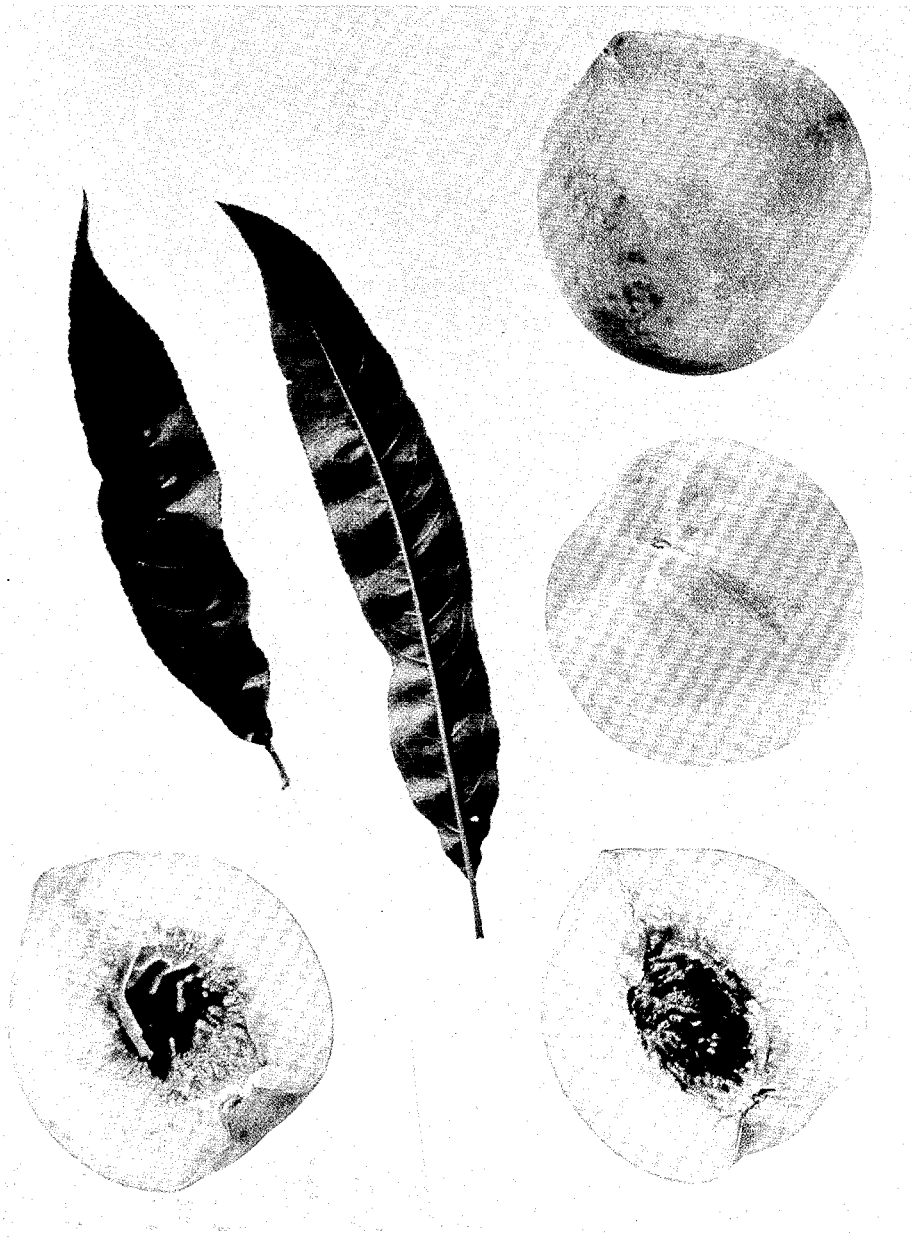
Inventor
H. C. Swim
By: Robb & Robb
Attorneys.

United States Patent Office

Plant Pat. 1,649
Patented Oct. 8, 1957

1,649

PEACH TREE

Herbert C. Swim, Ontario, Calif., assignor to Armstrong Nurseries, Inc., Ontario, Calif., a corporation of California Application November 6, 1956, Serial No. 620,778

1 Claim. (Cl. 47—62)

The present invention relates to a new and distinct variety of peach tree of the yellow-fleshed, freestone, fruit-bearing type, which was originated by me by crossing two unnamed and unpatented peach varieties with the view of combining the most desirable characteristics of the two parent varieties, and thus achieving a new and improved variety. This objective was fully achieved, as will hereinafter more clearly appear.

The seed parent of my new variety was characterized by its white-fleshed, freestone fruit of from medium to large size, with better than average red skin color, a sweet and delectable flavor, with a ripening period from early to mid-August in southern California. The tree of this parent was endowed with a vigorous habit of growth, good yielding habit, and required only medium chilling.

The pollen parent, on the other hand, was a yellow-fleshed, freestone fruit type of peach, the fruit of which was medium size, with good skin color, a good but rather acid flavor, and having a ripening period from middle to late June in southern California. This parent variety was further characterized by its heavy yielding ability and from a low to medium chilling requirenment.

The new variety which resulted from the aforementioned breeding is characterized by the following dominant features which represent a unique combination and distinguish the new variety from its parents, as well as from all other varieties of which I am aware:

(1) A vigorous tree growth and consistent production of large fruit crops each season;

(2) Very large, yellow-fleshed, freestone fruit;

(3) The outer surface of the fruit skin is overlaid with an attractive red blush, particularly on the side exposed to the sun;

(4) A fruit maturation period from peak bloom to tree-ripe approximately 4 or 5 days longer than that of the well-known standard variety "July Elberta" (Plant Patent No. 15), but because the new variety has a lower chilling requirement than "July Elberta" and a resultant earlier blooming habit, the new variety ripens from 5 to 10 days ahead of "July Elberta" in southern California, usually from early to mid-July; and (5) A low to medium winter chilling requirement, falling between the variety "Springtime" (Plant Patent No. 1268) and "Redwing" (Plant Patent No. 621), as observed in southern California.

In comparison with its unnamed seed parent, the fruit of my new variety ripens 3 or 4 weeks earlier; has yellow flesh instead of the white flesh of the parent; and has a more balanced sugar and acid flavor than the sweeter flavor of this parent.

As compared with its unnamed pollen parent, the fruit of my new variety ripens 2 or 3 weeks later; is larger in size; and has a more balanced sugar and acid flavor than the strongly acid fruit of this parent.

Asexual reproduction of the new variety by grafting, as performed at Ontario, California, shows that the foregoing characteristics and distinctions come true to form and are established and transmitted through succeeding propagations.

The accompanying drawing shows typical specimens of the foliage and fruit of my new variety, with both the upper and lower surfaces of the foliage being illustrated, and with both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart, except where color is given from Ridgway's Color Standards and Nomenclature (hereinafter abbreviated as "Ridgway"), or where general color terms of ordinary dictionary significance are obvious:

Dates first and last picking: Generally ripens from 5 to 10 days ahead of "July Elberta" in early to mid-July at Ontario, California, though over a prolonged period of observation, the dates of commencement of first ripening ranged from June 30th to July 20th, with ripening ending from July 10th to July 28th.

Tree: Large; vigorous; upright; dense; vase-formed; very productive; regular bearer.

*Trunk.*—From stocky to medium in caliper; medium surface roughness.

*Branches.*—From stocky to medium caliper; medium smoothness; dull. Color—near Rood's Brown, Plate XXVIII (Ridgway), overlaid heavily with near Light Grayish Olive, Plate XLVI (Ridgway). Lenticels—from numerous to medium in number; medium size.

*Leaves.*—Acuminate; lanceolate; medium thickness; relatively smooth; wavy type as described in publication by Meader and Blake entitled "Progress report on identification of peach varieties by leaf characteristics," appearing in American Society for Horticultural Science Proceedings for 1939, vol. 37, pages 203 to 207. Size—large; length—from 6 inches to 7½ inches; width—from 1½ inches to 2 inches. Color: upper surface—near Deep Dull Yellow-Green (1), Plate XXXII (Ridgway); under surface—near Chromium Green, Plate XXXII (Ridgway). Margin—finely serrate. Petiole—medium length; from ⅜ inch to ½ inch in length; from thick to medium thickness. Glands—average 4 in number; opposite; large; reniform; usually positioned on petiole below attachment of leaf blade, and also sometimes on leaf blade near attachment to petiole. Color—green.

*Stipules.*—Short; narrow; early deciduous.

Flower buds: From medium size to small; medium length; conic-pointed; bud scales with yellowish pubescence; free portion of calyx with grayish pubescence on outside surface.

Flowers:

*Dates first and full bloom.*—Over a prolonged period of observations, widely varied from February 8th to March 7th, and from February 17th to March 25th, respectively, due to weather variations from year-to-year; considered early to medium as compared with other varieties.

*Size.*—Small; non-showy type.

*Color (newly opened flower).*—Between Neyron Rose, Plate 623/1, page 76 and Phlox Pink, Plate 625/1, page 77.

Fruit:

*Maturity when described.*—Eating-ripe. Date—July 9th.

*Size.*—Only slightly variable; large. Axial diameter—from 2¾ inches to 3 inches. Transverse diameter in suture plane—from 2⅝ inches to 2⅞ inches. Diameter at right angles to suture plane—from 2¾ inches to 3 inches.

*Form.*—Uniform; symmetrical; globose.

*Suture.*—Usually an inconspicuous line; shallow; extends from base to apex; has slight depression beyond pistil point.

*Ventral surface.*—Rounded; sometimes slightly lipped on right or left sides, but often not lipped; lips slightly unequal.

*Cavity.*—From rounded to somewhat elongated in suture plane, with suture showing on one side. Depth—¼ inch. Breadth—from ½ inch to ⅝ inch.

*Base.*—Rounded.

*Apex.*—Short; rounded; with short apical pistil point.

*Stem.*—From ⅜ inch to ½ inch in length; stout; glabrous; strong adherence to stone.

*Skin.*—Medium thickness; medium texture; free. Tendency to crack—none. Color—between Lemon Yellow, Plate 4/2, page 4 and Buttercup Yellow, Plate 5/2, page 5, overlaid particularly on side exposed to the sun with between Delft Rose, Plate 020/1, page 108 and Delft Rose, Plate 020, page 108 and with Claret Rose, Plate 021, page 109. Down—moderate; from medium to short; rolls up when rubbed.

*Flesh.*—Color—between Buttercup Yellow, Plate 5/2, page 5 and Indian Yellow, Plate 6/2, page 6, with flecks and streaks or blotches of near Geranium Lake, Plate 20, page 20. Surface of pit cavity—color—near Geranium Lake, Plate 20, page 20, with fibres of near Indian Yellow, Plate 6/2, page 6. Amygdalin—scant. Juice—from abundant to moderate; rich. Texture—medium firmness; fine; melting. Fibres—medium number; fine; tender. Ripens—fairly evenly. Flavor—subacid. Aroma—pronounced. Eating quality—good.

Stone: Free; adheres to flesh along both dorsal and ventral edges; short fibres; free on sides; sometimes retains short fibres in furrows.

*Size.*—From large to medium. Length—from 1½ inches to 1⅝ inches. Breadth—from ⅞ inch to 1⅛ inches. Thickness—from ⅝ inch to ¾ inch.

*Form.*—Ovoid; cuneate towards apex.

*Base.*—Somewhat oblique.

*Hilum.*—Narrow; oblong.

*Apex.*—Acute.

*Sides.*—Very slightly unequal; curved on right and left sides.

*Surface.*—Irregularly furrowed towards apex; ridged towards apex; pitted from base to above center.

*Ridges.*—Usually rounded towards apex.

*Pits.*—Elongated.

*Ventral edge.*—From medium to thick; with wing throughout.

*Dorsal edge.*—Medium; with shallow, narrow groove to above center; ridges on either side interrupted.

*Tendency to split.*—None.

*Color.*—Between Sayal Brown, Plate XXIX (Ridgway) and Snuff Brown, Plate XXIX (Ridgway), with streaks of between Spectrum Red, Plate I (Ridgway) and Carmine, Plate I (Ridgway).

Use: Market; local; dessert.

Keeping quality: From good to medium.

Insect resistance: Medium resistance to thrips, as determined by comparison with other varieties grown under same cultural conditions at Ontario, California.

Disease resistance: No disease susceptibility observed at Ontario, California.

Shipping quality: From good to medium.

I claim:

A new and distinct variety of peach tree of the yellow-fleshed, freestone fruit-bearing type, substantially as herein shown and described, characterized particularly as to novelty by its vigorous growth and consistent production of large crops each season, the very large size of its fruit, the attractive red blush on the outer surface of the fruit skin particularly on the side exposed to the sun, its relatively long maturation period averaging approximately 4 or 5 days longer than that of the variety "July Elberta" (Plant Patent No. 15), its low to medium winter chilling requirement falling between that of the variety "Springtime" (Plant Patent No. 1268) and "Redwing" (Plant Patent No. 621) and even lower than that of "July Elberta," its resultant earlier blooming habit, and its earlier ripening habit averaging from 5 to 10 days earlier than "July Elberta" and falling from early to mid-July in southern California.

No references cited.